United States Patent [19]

Pasenok et al.

[11] Patent Number: 5,780,672
[45] Date of Patent: Jul. 14, 1998

[54] PROCESS FOR THE SELECTIVE PREPARATION OF MONOFLUORO DERIVATIVES

[75] Inventors: Sergej Pasenok, Liederbach; Wolfgang Appel, Kelkheim, both of Germany

[73] Assignee: Hoechst Aktiengesellschaft, Frankfurt, Germany

[21] Appl. No.: 678,734

[22] Filed: Jul. 11, 1996

[30] Foreign Application Priority Data

Jul. 14, 1995 [DE] Germany .................. 195 25 727.8

[51] Int. Cl.$^6$ .................. C07C 69/63; C07C 51/58; C07C 45/00; C07C 19/08
[52] U.S. Cl. .................. 560/227; 570/124; 570/127; 570/128; 549/518; 562/852; 568/484; 560/125; 560/145; 560/100; 560/105
[58] Field of Search .................. 560/227, 125, 560/145, 100, 105; 570/124, 127, 128; 549/518; 562/852; 568/484

[56] References Cited

U.S. PATENT DOCUMENTS

| | | | |
|---|---|---|---|
| 3,137,701 | 6/1964 | Ayer et al. | 260/285 |
| 4,833,250 | 5/1989 | Bay | 546/345 |
| 5,442,084 | 8/1995 | Lal | 558/141 |

FOREIGN PATENT DOCUMENTS

| | | |
|---|---|---|
| 0 187 023 | 7/1986 | European Pat. Off. . |
| 0251246 | 7/1988 | European Pat. Off. . |

OTHER PUBLICATIONS

Liotta et al., "The Chemistry of Naked ... Solvents", J. Am. Chem. Soc., 96:7, pp. 2250–2252, Apr. 1974.
Burton et al., "Tributylarsonium–2,2,3,3,4,4–hexa . . . Cleavage", J. Fluorine Chem., 18, pp. 413–416, Mar. 1981.
Burton et al., "Trialkylammonium–2,2,3,3,4,4 . . . Carbon-ion", J. Am. Chem. Soc., 99:14, pp. 4830–4831, Jul. 1977.
Rapp, "Reactions of Polyfluoro Olefins ... Triethylamine", J. Am. Chem. Soc., 73, pp. 5901–5902, Dec. 1951.
Tetrahedron, 1996; vol. 52 (8); pp. 2977–2982, Corporate Research: Hoechst AG; Frankfurt; D–65926; Germany (DE), XP002016770, Pasenok S.V. et al. "New Method of Preparation of Fluoro Compounds via Utilization of Ammonium and Phosponium Perfluorocyclobutane Ylides as Fluorination Reagents".
J.T. Welch, Tetrahedron, vol. 43, No. 14 (1987) p. 3123.
G.B. Spero, et al., Steroids, vol. 11, Jun (1968) p. 769.
W.G. Young, et al., J. Am. Chem. Soc., vol. 82 Dec. 5, (1960) p. 6163.
R.L. Pruett, et al., J. Am. Chem. Soc., vol. 74 Apr. 5, (1952) p. 1633.
K.E. Rapp, et al., J. Am. Chem. Soc., vol. 72 (1950) p. 3646.

Primary Examiner—Paul J. Killos
Assistant Examiner—Rosalynd Keys
Attorney, Agent, or Firm—Frommer Lawrence & Haug LLP

[57] ABSTRACT

A process for the preparation of compounds of the formula (1) in which $R^1$, $R^2$ and $R^3$ are as defined in the specification, which includes reacting alcohols or carboxylic acids of the formula (2) in which $R^1$, $R^2$ and $R^3$ are as defined in the specification, with a fluorinating agent of the formula (3) as defined in the specification.

6 Claims, No Drawings

PROCESS FOR THE SELECTIVE PREPARATION OF MONOFLUORO DERIVATIVES

The present invention relates to a process for the selective preparation of monofluoro derivatives.

It is known that fluorine has powerful and sometimes unexpected effects on the biological activity of chemical compounds. Replacing hydrogen or hydroxyl groups by fluorine in a biologically active molecule often leads to an analogous compound having increased or modified selectivity. This may be observed, in particular, in the case of steroids, alkaloids or amino acids (J. T. Welch, Tetrahedron V. 43, N 14, pp. 3123–3197, 1987).

The selective introduction of a fluorine atom into an organic molecule is therefore a valuable reaction for biological, mechanistic and structural studies and also for increasing the biological activity and chemical reactivity of such molecules.

The preparation of aliphatic monofluoro compounds by direct replacement of OH groups by fluorine is described, for example, by C. M. Sharts (Modern Methods to Prepare Monofluoroaliphatic Compounds, Org. Reactions, V.21, pp. 125–415).

It is further known that α,α-difluoroamines (fluoroamino reagents =FAR) are mild fluorination reagents which can replace hydroxyl groups by fluorine atoms. Thus reacting a primary alcohol or a carboxylic acid with the compounds (a) (Yarovenko reagent) or (b) (Ischikava reagent) usually gives a high yield of the desired monofluoro derivative with only a low proportion of by-products (N. N. Yarovenko et al., J. Gen. Chem. Engl. Trans., 29, 2125 (1959); R. L. Pruet et al. J. Am. Chem. Soc.,72, 3646, 1950).

$(C_2H_5)_2N-CF_2-CFHCl$ (a)

$(C_2H_5)_2N-CF=CF-CF_3 + (C_2H_5)_2N-CF_2-CFH-CF_3$ (b)

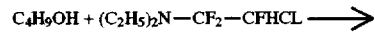

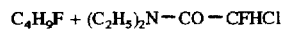

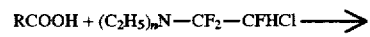

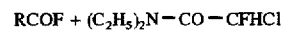

R = alkyl, phenyl

These methods are, in particular, suitable for the preparation of monofluoro derivatives of steroids, alkaloids and carbohydrates (G.B. Spero et al., Steroids, 11, 769, (1968); U.S. Pat. No. 3,137,701).

The use of α,α-difluoramines in preparative organic chemistry has a number of disadvantages, since these compounds are highly unstable and decompose within 2 days, which leads to great difficulties when they are employed in the laboratory and makes use in industry virtually impossible. Because of their instability during storage, α,α-difluoroamines are not commercially available (Org. React., B. 21, pp. 159). Furthermore, the reaction with alcohols or carboxylic acids produces the amides of the corresponding carboxylic acids, whose separation from the fluorinated products frequently poses problems, in particular in the case of alcohols or acid fluorides having high boiling points.

Known reagents for replacing OH groups for F are, e.g.: $SF_4$, $(C_2H_5)_2NSF_3$, $C_6H_5PF_4$, $(C_6H_5)_2PF_3$ and $(C_6H_5)_3PF_2$ (Y. Kobayashi et al., Chem. Pharm. Bull., 16,1009 (1968); W. C. Smith, J. Am. Chem. Soc., 82, 6167 (1960)). Substantial disadvantages of these reagents are their high toxicity and poor availability and the necessity to carry out the reaction under pressure in a closed system.

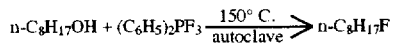

A further known method for the preparation of monofluoro derivatives starts from compounds such as KF, CsF or $(C_4H_9)_4NF$. However, these reagents are not capable of direct OH-F exchange, but only enable halogen atoms or sulfonic acid groups to be replaced by fluorine.

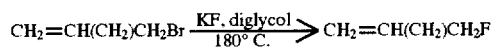

The object of the invention below is therefore to provide a process which enables OH groups of acids or alcohols to be selectively replaced by fluorine atoms and is free of the abovementioned disadvantages.

It has now been found that monofluoro derivatives of the formula (1) are obtained in a technically simple manner and in high yield and purity if OH derivatives of the formulae (2) or (3) are reacted with ammonium, arsonium or phosphonium ylides of the formula (4).

The present invention thus relates to a process for the preparation of compounds of the formula (1)

in which $R^1$, $R^2$ and $R^3$ independently of each other are H, $C_1$–$C_{12}$-alkyl, $PhCH_2$,$CH_2$=CH—$CH_2$, $C_5$–$C_7$-cycloalkyl, $C_6$–$C_{12}$-aryl, $C_6F_5$—, —$CO_2C_2H_5$ or where two of the radicals $R^1$, $R^2$ or $R^3$ together are =O, which comprises reacting alcohols or carboxylic acids of the formula (2)

in which $R^{1'}$, $R^{2'}$ and $R^{3'}$ independently of each other are H, $C_1$–$C_{12}$-alkyl, $PhCH_2$, $CH_2$=CH—$CH_2$, $C_5$–$C_7$-cycloalkyl, $C_6$–$C_{12}$-aryl, $C_6F_5$—, —$CO_2C_2H_5$ where two of the radicals $R^{1'}$, $R^{2'}$ or $R^{3'}$ together are =O, with a fluorinating agent of the formula (3)

where X=P, N, $P(NR_2)_3$ or As and
R=$C_1$–$C_4$-alkyl.

The reaction can be carried out in a solvent or in the absence of solvent. Solvents which can be used according to the invention are all organic solvents which are inert under the reaction conditions, e.g. dichloromethane, chloroform, tetrahydrofuran, acetonitrile, diethyl ether, diisopropyl ether, hexane or benzene.

The reaction temperature is generally in the range from 0° C. to 100° C., preferably in the range from 0° to 70° C.

The reaction time is 1 to 12 hours, in particular 1 to 6 hours.

The stoichiometric ratio of compounds of the formula (2) to compounds of the formula (3) is according to the invention 1:0.6 to 1:2.

After the reaction is completed, the product is distilled off in vacuo (1mm Hg) into a cold trap for low-boiling fluorine derivatives or extracted with, for example, ether or dichloromethane, washed with water, then dried and the solvent is removed.

In the reaction with alcohols, yields in the range from 60 to 80% are obtained. In the reaction with acids, the yields of acyl fluorides are in the range from 80 to 95%, in particular in the range from 85 to 90%.

The preparation of compounds of the formula (3) is known (R. L. Pruet et al., J. Am. Chem. Soc., 74, 1633 (1952)). Compounds which can act as starting compounds are, e.g. hexafluorocyclobutene and the corresponding nitrogen, phosphorus or arsenic compound. Ylides of the formula (3) have already been used for the synthesis of dioxocyclobetaines.

Examples of suitable N, P or As starting compounds are: trimethyl-triethyl- and tributylamines and tris(diethylamino) phosphines or triethylarsines.

Examples of highly reactive compounds of the formula (2) are: methanol, butanol, 2-butanol, benzyl alcohol, allyl alcohol, 3-phenyl-1-propanol, methyl α-hydroxyisobutyrate, benzoic acid, pentafluorobenzoic acid and acetic acid.

The starting compounds are generally reacted with one another for 1 to 6 hours at a temperature in the range from 0° to 50° C.

According to the process of the invention, it is surprising that ylides of the formula (3) are able to replace OH groups by F, since, according to the known prior art, replacement of F by the OR groups would be expected (R. L. Pruet et al., J. Am. Chem. Soc., 74, 1633 (1952).

The process of the invention has a number of advantages, thus, for example, fluorinating agents of the formula (3), in contrast to α,α-difluoro-amines, are stable over a long period in the absence of moisture. In addition, the fluorinating agents (3) used according to the invention may be synthesized in a simple manner and in high yields by reacting the tertiary amines or the corresponding phosphorus or arsenic compounds with the readily available perfluorocycloalkenes.

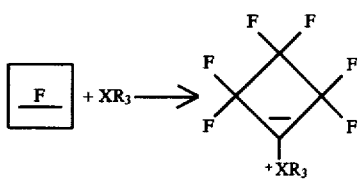

A further advantage of the present process is that the reaction products (4) obtained after the fluorination reaction are produced as sparingly soluble compounds having high melting points, which enables a simple separation of the desired monofluoro derivatives.

Compounds of the formula (1) are, as already mentioned at the outset, valuable precursors in the preparation of biologically active compounds. In addition, these compounds can be used as synthons for the preparation, for example of fluorine-containing heterocycles and colorants.

EXAMPLES

Example 1

Synthesis of triethylammonium-2,2,3,3,4,4-hexafluorocyclobutane ylide 16.2g (0.1 mol) of perfluorocyclobutene and 10.1g(0.1 mol) of triethylamine are charged into a pressure vessel and reacted for 6 hours at 0° C. The precipitate is dried in vacuo.

Yield: 92% m.p.: 105°–107° C. (decomposition)

EXAMPLE 2

Synthesis of tris(diethylamino)phosphonium-2,2,3,3,4,4-hexafluorocyclobutane ylide 24.7 g (0.1 mol) of tris(diethylamino)phosphine in 50 ml of diethyl ether are introduced into a three-necked flask with dry ice and cooler and 17.8 g (0.11 mol) of perfluorocyclobutene are added at −30° C. The reaction mixtue is stirred for 1 hour at −30° C and the solvent is distilled off in vacuo.

Yield: 95% m.p.: 110°–112° C.

EXAMPLE 3

Benzoyl fluoride 0.1 mol of benzoic acid in 100 ml of dichloromethane is introduced into a three-necked flask having a thermometer and bubble counter and 0.06 mol of triethylammonium-2,2,3,3,4,4-hexafluorocyclobutane ylide is added in the absence of moisture. The reaction mixture is stirred for one hour at room temperature and for 2 hours at 40° C. The solvent and benzoyl fluoride are condensed into a cold trap in vacuo (1 mm Hg). CH$_2$Cl$_2$ is distilled off and the product is purified by distillation in vacuo.

Yield: 93%

Boiling point: 48° C. /20 mbar

EXAMPLE 4

Pentafluorobenzoyl fluoride

The synthesis was performed analogously to Example 3 starting from pentafluorobenzoic acid.

Yield: 98%

Boiling point: 50°–53° C. /24 mbar

EXAMPLE 5

Acetyl fluoride

The synthesis was performed analogously to Example 3, starting from acetic acid.

Yield: 81%

Boiling point: 21°–22° C.

EXAMPLE 6

Benzyl fluoride 0.15 mol of triethylammoniumhexafluorocyclobutane is added in the absence of moisture to a solution of 0.1 mol of benzyl alcohol in 100 ml of dichloromethane. The reaction mixture is stirred for 2 hours at room temperature and then for 2 hours at 40° C. After the reaction is completed, the reaction mixture is condensed over into a cold trap, in order to separate off dioxobetaines produced. The solvent is distilled off at atmospheric pressure and the product is purified by vacuum distillation.

Yield: 72%

Boiling point: 60° C. /20 mbar

EXAMPLE 7

2-Fluorobutane

The synthesis was performed analogously to Example 6 without solvent, starting from 2-butanol.

Yield: 68%

Boiling point: 20°–24° C.

EXAMPLE 8

Octyl fluoride

The synthesis was performed analogously to Example 6, starting from octanol.

Yield: 63% boiling point: 143° C.

We claim:

1. A process for the preparation of compounds of the formula (1)

  (1)

in which $R^1$, $R^2$ and $R^3$ independently of each other are H, $C_1$–$C_{12}$-alkyl, $PhCH_2$, $CH_2$=CH—$CH_2$, $C_5$–$C_7$-cycloalkyl, $C_6$–$C_{12}$-aryl, $C_6F_5$—, —$CO_2C_2H_5$ or where two of the radicals $R^1$, $R^2$ or $R^3$ together are =O which comprises reacting alcohols or carboxylic acids of the formula (2).

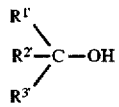  (2)

in which $R^{1'}$, $R^{2'}$ and $R^{3'}$ independently of each other are H, $C_1$–$C_{12}$-alkyl, $PhCH_2$, $CH_2$=CH=$CH_2$, $C_5$–$C_7$-cycloalkyl, $C_6C_{12}$-aryl, $C_6F_5$—, —$CO_2C_2H_5$ or where two of the radicals $R^{1'}$, $R^{2'}$ or $R^{3'}$ together are =O with a fluorinating agent of the formula (3)

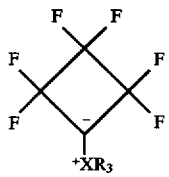  (3)

where X=P, N, $P(NR_2)_3$ or As and R=$C_1$–$C_4$-alkyl.

2. The process as claimed in claim 1, wherein the reaction temperature is in the range from 0° to 70° C.

3. The process as claimed in claim 1, wherein the reaction time is in the range from 1 to 12 hours.

4. The process as claimed in claim 1, wherein the ratio of the compounds of the formula (2) to compounds of the formula (3) is in the range from 1:0.6 to 1:2.

5. A method for preparing a fluorinated derivative of a biologically active compound which comprises preparing a compound of the formula (1)

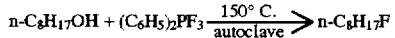

$R^1$, $R^2$ and $R^3$ independently of each other are H, $C_1$–$C_{12}$-alkyl, $PhCH_2$, $CH_2$=CH—$CH_2$, $C_5$–$C_7$-cycloalkyl, $C_6$–$C_{12}$-aryl, $C_6F_5$—, —$CO_2C_2H_5$ or where two of the radicals $R^1$, $R^2$ or $R^3$ together are =0, which comprises reacting alcohols or carboxylic acids of the formula (2)

  (2)

in which $R^{1'}$, $R^{2'}$ and $R^{3'}$ independently of each other are H, $C_1$–$C_{12}$-alkyl, $PhCH_2$, $CH_2$=CH—$CH_2$, $C_5$–$C_7$-cycloalkyl, $C_6$–$C_{12}$-aryl, $C_6F_5$—, —$CO_2C_2H_5$ or where two of the radicals $R^{1'}$, $R^2$ or $R^3$ together are =O, with a fluorinating agent of the formula (3)

  (3)

where X=P, N, $P(NR_2)_3$ or As and
R=$C_{1-C_4}$-alkyl, and contacting the compound of the formula (1) with the biologically active compound.

6. A method for preparing a fluorine containing derivative of a heterocycle or colorant which comprises preparing a compound of the formula (1)

  (1)

in which $R^{1, R2}$ and $R^3$ independently of each other are H, $C_1$–$C_{12}$-alkyl, $PhCH_2$, $CH_2$=CH—$CH_2$, $C_5$–$C_7$-cycloalkyl, $C_6$–$C_{12}$-aryl, $C_6F_5$—, —$CO_2C_2H_5$ or where two of the radicals $R_1$, $R^2$ or $R^3$ together are =O, which comprises reacting alcohols or carboxylic acids of the formula (2)

  (2)

in which $R^{1'}$, $R^{2'}$ and $R^{3'}$ independently of each other are H, $C_1$–$C_{12}$-alkyl, $PhCH_2$, $CH_2$=CH—$CH_2$, $C_5$–$C_7$,-cycloalkyl, $C_5$–$C_{12}$-aryl, $C_6F_5$—, —$CO_2C_2H_5$ or where two of the radicals $R^{1'}$, $R^{2'}$ or $R^{3'}$ together are =O, with a fluorinating agent of the formula (3)

  (3)

where X=P, N, $P(NR_2)_3$ or As and
R=$C_1$–$C_4$-alkyl, and contacting the compound of the formula (1) with the heterocycle or colorant.

* * * * *